US007519591B2

(12) United States Patent
Landi et al.

(10) Patent No.: US 7,519,591 B2
(45) Date of Patent: Apr. 14, 2009

(54) SYSTEMS AND METHODS FOR ENCRYPTION-BASED DE-IDENTIFICATION OF PROTECTED HEALTH INFORMATION

(75) Inventors: William A. Landi, Devon, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 427 days.

(21) Appl. No.: 10/796,255

(22) Filed: Mar. 9, 2004

(65) Prior Publication Data
US 2005/0165623 A1  Jul. 28, 2005

Related U.S. Application Data

(60) Provisional application No. 60/454,114, filed on Mar. 12, 2003.

(51) Int. Cl.
G06F 7/00 (2006.01)
G06F 17/30 (2006.01)
G06F 17/00 (2006.01)
(52) U.S. Cl. .............................. 707/6; 707/9; 707/104.1
(58) Field of Classification Search ...................... 707/1, 707/9, 100, 102, 103 R, 6, 10, 104.1, 200; 713/109, 193; 705/2, 3, 51; 726/26, 27
See application file for complete search history.

(56) References Cited

U.S. PATENT DOCUMENTS

| | | | | |
|---|---|---|---|---|
| 5,956,400 A | * | 9/1999 | Chaum et al. | 713/167 |
| 6,823,203 B2 | * | 11/2004 | Jordan | 600/407 |
| 6,874,085 B1 | * | 3/2005 | Koo et al. | 713/165 |
| 7,039,810 B1 | * | 5/2006 | Nichols | 713/182 |
| 7,158,979 B2 | * | 1/2007 | Iverson et al. | 707/100 |
| 7,181,017 B1 | * | 2/2007 | Nagel et al. | 380/282 |
| 2001/0054155 A1 | * | 12/2001 | Hagan et al. | 713/193 |
| 2002/0116227 A1 | * | 8/2002 | Dick | 705/3 |
| 2003/0021417 A1 | * | 1/2003 | Vasic et al. | 380/277 |
| 2003/0088771 A1 | * | 5/2003 | Merchen | 713/175 |
| 2004/0143594 A1 | * | 7/2004 | Kalies | 707/103 R |
| 2004/0172293 A1 | * | 9/2004 | Bruschi et al. | 705/2 |

OTHER PUBLICATIONS

"Digital Imaging and Communications in Medicine (DICOM)—Supplement 55: Attribute Level Confidentiality (Including De-identifciation)", *DICOM Standards Committee, Working Group 14 Security*, Sep. 5, 2002.

* cited by examiner

*Primary Examiner*—Don Wong
*Assistant Examiner*—Merilyn P Nguyen (57) ABSTRACT

Systems and methods are provided for protecting individual privacy (e.g., patient privacy) when individual data records (e.g., patient data records) are shared between various entities (e.g., healthcare entities). In one aspect, systems and methods are provided which implement secured key encryption for de-identifying patient data to ensure patient privacy, while allowing only the owners of the patient data and/or legally empowered entities to re-identify subject patients associated with de-identified patient data records, when needed.

33 Claims, 3 Drawing Sheets

SYSTEMS AND METHODS FOR ENCRYPTION-BASED DE-IDENTIFICATION OF PROTECTED HEALTH INFORMATION

CROSS-REFERENCE TO RELATED APPLICATION

This application claims priority to U.S. Provisional Application Ser. No. 60/454,114, filed on Mar. 12, 2003, which is fully incorporated by reference.

TECHNICAL FIELD OF THE INVENTION

The present invention relates, in general, to systems and methods for protecting patient privacy when health care information is shared between various healthcare entities and, in particular, to systems and methods that implement secured key encryption for de-identifying patient data to ensure patient privacy, while allowing only the owners of the patient data records and/or other legally empowered entities to re-identify subject patients of de-identified data records, when needed.

BACKGROUND

Due to continued technological advancements in data storage systems and information processing systems, health care providers and organizations continue to migrate toward environments where most aspects of patient care management are automated, making it easier to collect and analyze patient information. Consequently, health care providers and organizations, etc., tend to accumulate vast stores of patient information, such as financial and clinical information, in the form of electronic patient data records that are stored in electronic databases or other electronic medium such as files. In this document, the term database is used as a general term to denote any mechanism for storing data electronically and is not limited to a traditional database system. Such patient information may be stored in a myriad of unstructured and structured formats, and includes many items of patient identifying information that can be used to identify subject patients of the patient data records.

There are various circumstances in which healthcare organizations have to disclose or otherwise share their patient data with other healthcare entities, agencies, business partners, etc. However, healthcare organizations have both an ethical and legal responsibility for protecting patient privacy. Organizations cannot release or otherwise disclose patient data records that contain patient identifying information that can be used to identify patients without patient approval unless there is a valid reason as defined by various laws and regulations. For example, valid reasons are generally related to TPO, treatment, payment, and operations but can also cover other activities such as certain research. Even when a valid reason exists, there is still an obligation on the part of the organization to release only the minimum amount of information that is necessary for the particular reason.

In the United States, standards such as HIPAA (Health Insurance Portability and Accountability Act) have resulted in Federal regulations that place strict requirements on the archiving and disclosure of medical records. For example, in accordance with HIPAA, Federal regulations have been promulgated requiring healthcare organizations and physicians to ensure the protection, privacy and security of patient medical information. In particular, the "Privacy Rule" of HIPAA provides Federal privacy regulations that set forth requirements for confidentiality and privacy policies and procedures, consents, authorizations and notices, which must be adopted in order to maintain, use, or disclose individually identifiable health information in treatment, business operations or other activities.

The HIPAA Privacy Rule allows for certain entities to "de-identify" protected health information for certain purposes so that such information may be used and disclosed freely, without being subject to the protections afforded by the Privacy Rule. The term "de-identified data" as used by HIPAA refers to patient data from which all information that could reasonably be used to identify the patient has been removed (e.g., removing name, address, social security numbers, etc . . . ). The Privacy Rule requirements do not apply to information that has been de-identified. HIPAA also defines the notion of "Limited Data Set" which is "de-identified data" but the de-identification requirements are not as stringent. Further, the distribution requirements on limited data sets are tighter than those for more completely de-identified data.

Conventional methods for de-identifying patient data include simply stripping all information from the patient data records that can be used to determine the identity of a patient, or replacing such patient identifying information with something else (e.g. replace the actual name with the string "name"). With such methods, although the patient data records are de-identified, there is no mechanism by which patient identification can be recovered, if necessary.

SUMMARY OF THE INVENTION

Exemplary embodiments of the invention generally include systems and methods for protecting individual privacy (e.g., patient privacy) when private information (e.g., health care information) is shared between various entities (e.g., healthcare entities). More specifically, exemplary embodiments of the invention include systems and methods that implement secured key encryption for de-identifying patient data to ensure patient privacy, while allowing only the owners of the patient data and/or legally empowered entities to re-identify subject patients associated with de-identified patient data records, when needed.

In one exemplary embodiment of the invention, a method for processing data includes the steps of obtaining a data record of an individual which includes individual identifying information, removing the individual identifying information in the data record to generate a de-identified data record, generating an encrypted ID for the individual, wherein the encrypted ID comprises an encrypted representation of one or more items of individual identifying information, and storing the encrypted ID with or in the de-identified data record. A decryption key is securely maintained and accessible by an authorized entity that is legally authorized or empowered to decrypt the encrypted ID in the de-identified data record to re-identify the individual.

In one exemplary embodiment of the invention, the data records are patient data records containing clinical and possibly financial (billing) information. In other embodiments of the invention, the data records may comprise, e.g., financial records, employer/employee records, appraisals, student records, etc.

In another exemplary embodiment of the invention, a system for processing data includes a first data processing system, a second data processing system and a third data processing system. The first data processing system comprises a first repository that stores data records of an individual which include individual identifying information, and an encryption system that can generate an encrypted ID for the individual using an encryption key associated with the first data processing system, wherein the encrypted ID comprises an encrypted representation of one or more items of individual identifying information, and wherein the encryption system can generate de-identified data records of the individual which are associated with the encrypted ID. The second data processing system comprises a second repository that stores de-identified data records generated by the first data processing system and an engine that can process the de-identified data records in the second repository. The third data processing system comprises a third repository that stores a master decryption key, and an encryption system that can use the master decryption key to decrypt an encrypted ID of de-identified data records to re-identify an individual.

These and other exemplary embodiments, aspects, features and advantages of the present invention will become apparent from the following detailed description of exemplary embodiments, which is to be read in connection with the accompanying drawings.

DETAILED DESCRIPTION OF EXEMPLARY EMBODIMENTS

In general, exemplary embodiments of the invention as described herein include systems and methods for protecting patient privacy when patient health care information is shared between various entities. More specifically, systems and methods according to the invention implement a secured encryption protocol that enables de-identification of patient data in a manner that protects patient privacy, while allowing owners of the patient data and/or legally empowered entities, to re-identify subject patients that are associated with de-identified patient data records, when needed or desired. For example, depending on the application, a secured encryption protocol for de-identifying and re-identifying patient data may be implemented using an asymmetric or symmetric key encryption method. Advantageously, as explained below, systems and methods according to the invention for de-identifying/re-identifying patient data can be implemented for various purposes such as research, public health or healthcare operations, while maintaining compliance with regulations based on HIPAA for protecting patient privacy.

It is to be understood that the exemplary systems and methods described herein in accordance with the present invention may be implemented in various forms of hardware, software, firmware, special purpose processors, or combinations thereof. In one exemplary embodiment of the invention, the exemplary systems and methods described herein are implemented in software as an application comprising program instructions that are tangibly embodied on one or more program storage devices (e.g., hard disk, magnetic floppy disk, RAM, CD Rom, DVD, ROM and flash memory), and executable by any device or machine comprising suitable architecture. It is to be further understood that because the constituent system modules and method steps depicted in the accompanying Figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

Figure 1:
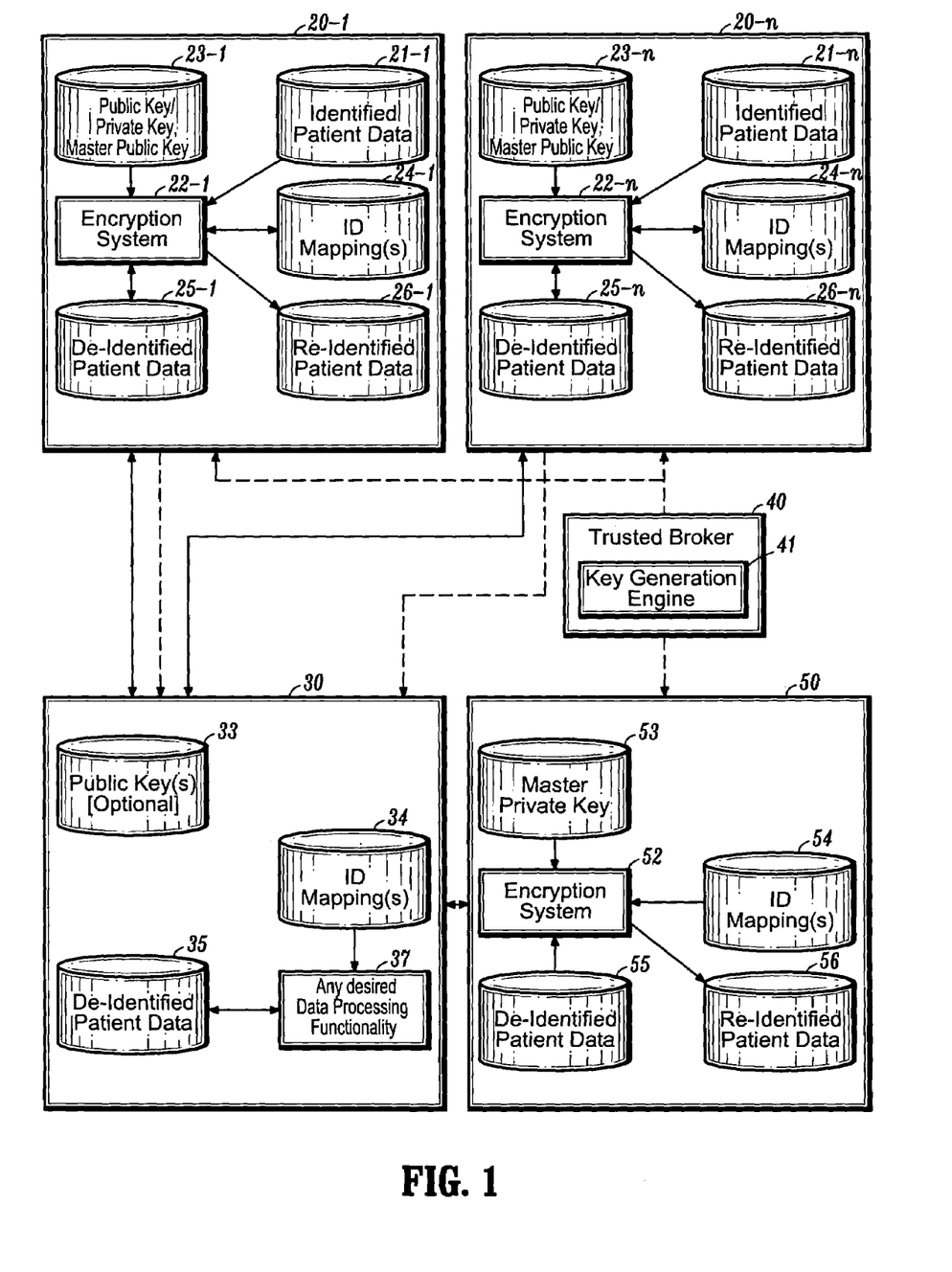
FIG. 1 illustrates a high-level schematic diagram of a system according to an exemplary embodiment of the invention, which employs secured key encryption to protect patient privacy when patient data is shared between different entities.

FIG. 1 illustrates a high-level schematic diagram of a system (10) according to one exemplary embodiment of the invention wherein a secured encryption scheme is implemented for protecting patient privacy when patient data is shared between different entities. In general, the exemplary system (10) comprises a plurality of patient data processing systems (20-1~20-n), a central patient data processing system (30), a trusted broker system (40), and a central surveillance system (50). The patient data processing systems (20-1~20-n) are operated at different clinical sites by different healthcare organizations (including, but not limited to, doctors, health care providers, institutions, associations, organizations, hospitals, etc.). In the exemplary embodiment, each clinical cite releases de-identified patient data records to a third-party entity that operates the central patient data processing system (30), wherein the collected de-identified data records can be processed for purposes of, e.g., research, health care monitoring, etc. In addition, the central surveillance system (50) may be operated and controlled by a governmental agency (such as the CDC), or any other entity that is authorized by laws or regulations for example, to re-identify subject patients that are associated with de-identified patient data records maintained and processed by the central patient data processing system (30).

Furthermore, in the exemplary embodiment of FIG. 1, the system (10) is implemented using a asymmetric encryption scheme (e.g., RSA) for protecting patient privacy, wherein de-identification and re-identification of patient data is implemented using public key/private key pairs that are generated for different healthcare entities. As explained in further detail below, the public keys (which are generated based on one or more private keys) are used for de-identifying (encrypting) one or more items of patient identifying information (i.e., information that could be used for identifying the patient) to generate an encrypted version of the patient identifying information (referred to herein as "Encrypted IDs") and the private keys are used for decrypting de-identified patient data to re-identify subject patients.

In the exemplary embodiment of FIG. 1, each patient data processing system (20-1~20-n) respectively comprises persistently stored electronic patient data records (21-1~21-n) that contain identified patient data, an encryption system (22-1~22-n), and optional securely stored encryption keys (23-1~23-n). In addition, each patient data processing system (20-1~20-n) may optionally store data structures (24-1~24-n) such as index or map structures, which, as explained below, can be used for mapping "Encrypted IDs " to "Study IDs", a repository of persistently stored de-identified data records (25-1~25-n) (to optionally store de-identified data that is provided to the central data processing system (30)) and a repository of persistently stored re-identified data (26-1~26-n) to optionally store re-identified patient data that is generated, when needed, using a corresponding private (decryption) key and the de-identified data.

In one exemplary embodiment of the invention, each encryption system (22-1~22-n) implements the same secure public encryption protocol (e.g., RSA). Depending on the application, however, the encryption systems (22-1~22-n) may perform one or more functions. For example, according to one exemplary embodiment of the invention, the encryption systems (22-1~22-n) may include methods for encrypting patient identifying information that is stored in (or stored with) the patient data records (21-1~21-n) using respective public keys and/or a master public key (23-1~23-n). More specifically, each healthcare entity can use its own public key or both its own public key and the master key to encrypt one or more items of patient identifying information contained in the respective patient medical records owned/managed by the healthcare entity), to thereby generate an Encrypted ID for each subject patient. An Encrypted ID of a given patient is a unique reproducible encrypted version of patient identifying information that is sufficient to uniquely identify the patient. The patient identifying information, which is encrypted to generate the Encrypted ID, may include one or more items of patient identifying information, including, but not limited to, patient name, social security number, and/or address.

If a particular entity only uses its public key to encrypt patient identifying information, then only the entity's corresponding private key can be used to decrypt the de-identified data. If a particular entity only uses the master public key to encrypt the patient identifying information, then only a master private key (e.g., a master private key (53) of the surveillance system (50)) can be used to decrypt the de-identified data. On the other hand, if a particular entity uses both its public key and the master public key to encrypt the patient identifying information, then either the entity's corresponding private key or the master private key can be used to decrypt the de-identified data.

The encryption systems (22-1~22-n) can operate to generate Encrypted IDs and then store each Encrypted ID with or within a corresponding de-identified data patient data record (i.e., a patient data records from which patient identifying information has been removed). In this regard, each data processing system (20-1~20-n) may comprise a repository of persistently stored de-identified patient data records (25-1~25-n) which include de-identified data patient data records having corresponding Encrypted IDs stored in or with the de-identified records. The encrypted (de-identified) patient data (Encrypted IDs) can be included in de-identified patient records, which can be released to third-party entities without compromising patient privacy. In general these records would be removed from the data processing system (20-1~20-n) after transfer to the central patient data processing system (30).

It is to be understood that the process of removing patient identifying information from patient records can be performed manually, or using automated methods according to the invention. For example, a de-identified data record for a given patient may be generated by an authorized user who manually removes patient identifying information from a data record and then uses the encryption system to generate an Encrypted ID for the subject patient, which is associated with the de-identified data record.

Figure 2:
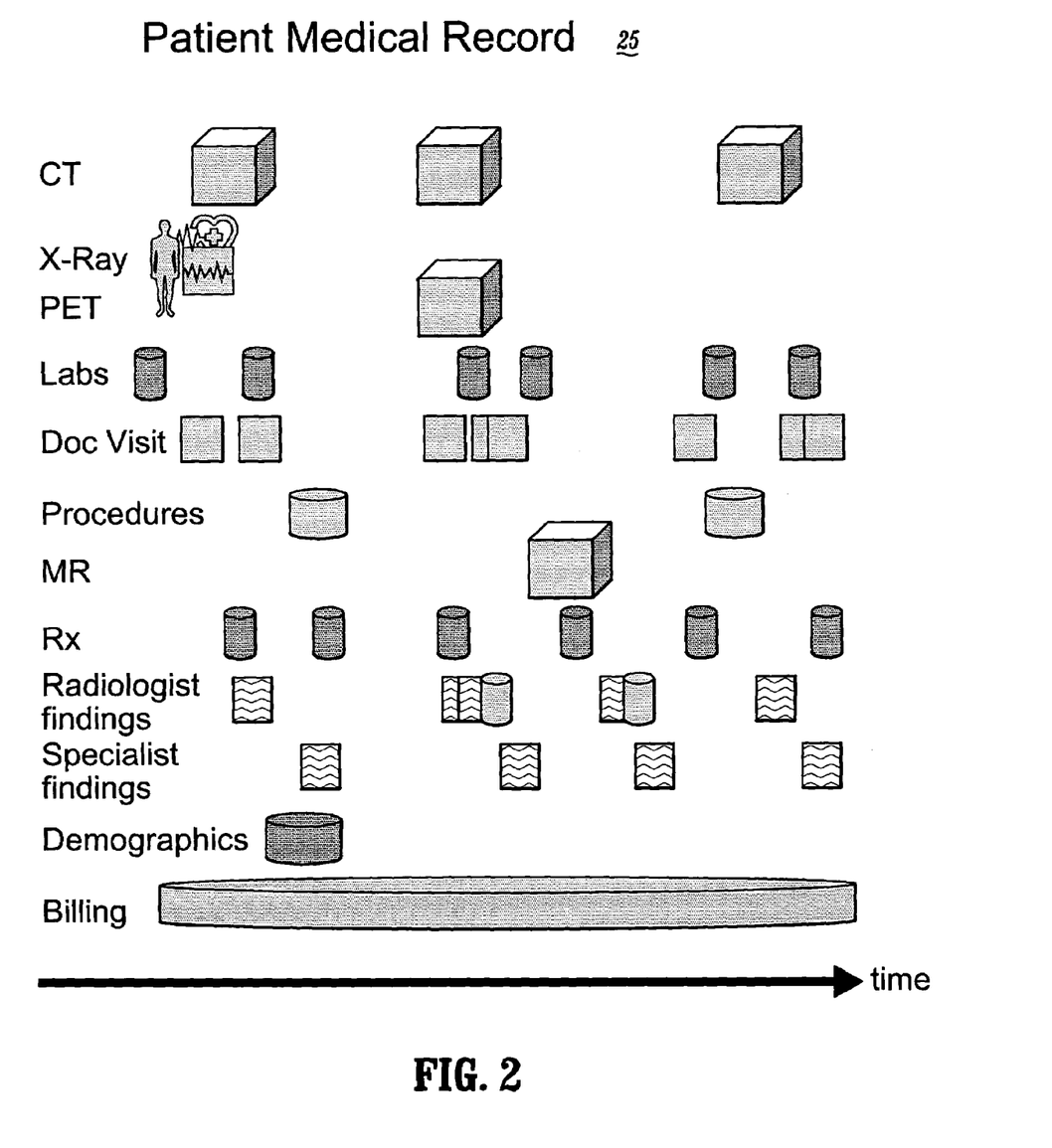
FIG. 2 illustrates an exemplary electronic patient medical record comprising a plurality of structured and unstructured data sources containing patient identifying information, which can be automatically de-identified using systems and methods according to exemplary embodiments of the invention.

Further, in another exemplary embodiment of the invention, the encryption systems (22-1~22-n) may include methods for automatically de-identifying a patient data record by automatically removing patient identifying information from the patient data records. More specifically, the encryption systems (22-1~22-n) may include methods for automatically de-identifying structured and/or unstructured patient data records that are included in the persistently stored electronic patient data records (21-1~21-n). By way of example, FIG. 2 illustrates an exemplary embodiment of the electronic patient data records (21-1~21-n) in the form of computerized patient records (CPR) (or electronic patient medical records) including a plurality of structured and unstructured data sources for maintaining patient information that can be collected over the course of patient treatments. The patient information may include, e.g., computed tomography (CT) images, X-ray images, laboratory test results, doctor progress notes, details about medical procedures, prescription drug information, radiological reports, other specialist reports, demographic information, and billing (financial) information. In general, the structured data sources include, for example, financial, laboratory, and pharmacy databases, wherein patient information in typically maintained in database tables. The unstructured data sources include for example, free-text based documents (e.g., physician reports, etc.) and images and waveforms data. Various methods for automatically de-identifying structured and unstructured data will be discussed in detail below with reference to FIG. 3, for example.

Referring again to FIG. 1, the encryption systems (22-1~22-n) may further include methods for mapping "Encrypted IDs " to "Study IDs" and replacing de-identified patient information in de-identified patient data records with human readable strings (as opposed to encrypted strings. As noted above, an Encrypted ID is generated by encrypting one or more items of patient identification information using a public key, and the Encrypted ID is included with or within a de-identified data record. However, the encrypted patient information in a de-identified patient data record would include a character string (e.g., a 128+ character string) that could make difficult or burdensome for a person to review the de-identified data record. Accordingly, a de-identification process according to an embodiment of the invention includes a method for replacing de-identified patient information with user-friendly character strings that contain no patient information.

More specifically, in one exemplary embodiment of the invention, a unique Encrypted ID (e.g., 128+ non-readable character string) of a given patient can be arbitrarily mapped to a Study ID that does not provide patient information, which is mapped in turn to one or more human readable, short replacement text strings that can be used for replacing de-identified patient data that is associated with the Encrypted ID. For example, given an arbitrary unique Encrypted ID that is mapped to a Study ID such as "42", text strings such as "patient 42 ID", "patient 42 name", "patient 42 address", etc . . . could be used to replace the various pieces of de-identified patient data in a de-identified data record. This association and human friendly replacement are optional and not required. In the system of FIG. 1, the persistently stored ID mappings (24-1~24-n) comprise data structures that map Encrypted IDs to Study IDs and corresponding replacements strings. Since these ID mappings (24-1~24-n) contain no patient information, that can be made publicly available to the third-party entity and stored in the database (35) without compromising patient privacy.

Furthermore, according to another exemplary embodiment of the invention, the encryption systems (22-1~22-n) may further include methods for re-identifying subject patients by using the appropriate private key to decrypt de-identified patient data that is contained in de-identified patient data records (25-1~25-n). For example, as depicted in FIG. 1, each of the healthcare entities that release de-identified patient data records can securely store a respective private key (23-1~23-n) for purposes of re-identifying patient data that was decrypted using their respective public key. During a re-identification process, if de-identified data records contain one or more Study IDs, the encryption systems (22-1~22-n)

can utilize the respective ID mapping(s) (24-1~24-n) to obtain the corresponding Encrypted IDs to be decrypted.

The central patient data processing system (30) comprises a repository of persistently stored de-identified patient data records (35) containing de-identified (encrypted) patient identifying information, which are collected from the different clinical sites. The central patient data processing system (30) comprises one or more data processing engines (37) that are used for processing the de-identified patient data (35) for one or more given applications. The central patient data processing system (30) includes a repository of ID mappings (34), which includes a collection of the ID mappings (23-14-n) associated with the individual data processing systems (20-10-n). The information contained the repository of ID mappings (34) is used by the data processing engine(s) (37) when processing the de-identified data records (35). Although only one central data processing system (30) is shown in FIG. 1, it is to be understood that in other embodiments of the invention, depending on the application, two or more similar central data processing systems (30) may be implemented.

In the exemplary embodiment of FIG. 1, it is assumed that the entity (or entities) that operate the central patient data processing system (30) does not have the authority to re-identify subject patients that are associated with the de-identified patient data records (35). In other words, the central patient data processing system (30) does not include an encryption system that is capable of decrypting Encrypted IDs that are stored in or with the de-identified patient data records (35). The central data processing system (30) may optionally maintain a repository of public keys that are associated with one or more of the entities that provide the de-identified patient data records (35) and associated ID mappings (34). However, since the central processing system (30) is not authorized to re-identify subject patients, the system (30) does not store (or cannot access) private keys that are associated with the one or more entities that provide the de-identified patient data records (35).

The central surveillance system (50) comprises a repository of de-identified patient data records (55) and corresponding ID mapping(s) (54), which can be obtained from the central data processing system (30) or the different entities that operate the data processing systems (20-1~20-n). In the exemplary embodiment of FIG. 1, it is assumed that the central surveillance system (50) is operated by one or more entities that are legally authorized or empowered to re-identify subject patients associated with the de-identified data records (55). In this regard, the central surveillance system (50) comprises an encryption system (52) and securely stored master encryption keys (53) (one key that can re-identify any institutions data), which can be used for decrypting de-identified patient data (Encrypted IDs) associated with the de-identified patient data records (55) using the ID mappings (54), if necessary. More specifically, the master private key (53) is a decryption key that can be used to decrypt de-identified data that is produced from many encryption/decryption key pairs in conjunction with its corresponding master public key. The encryption scheme is such that the encryption/decryption key pairs can be produced at any time, including, at the time of creation of the master private key or any time thereafter. In this manner, the master private key will remain valid as more and more clinical sites are issued public/private key pairs and added to the system (10) to provide de-identified patient data records.

Although one central surveillance system (50) is shown in FIG. 1, two or more surveillance systems may be implemented depending on the application. Moreover, in another exemplary embodiment of the invention, the central data processing system (30) and the central surveillance system (50) may be combined into one system, if that is appropriate from the perspective of privacy laws and regulations.

In the exemplary system (10) of FIG. 1, the trusted broker (40) (or certification agency (CA)) may be a third party entity that provides a trusted service for generating the encryption keys via a key generation engine (41), which are securely disseminated to the appropriate entities for purposes of de-identifying and re-identifying patient data. In other exemplary embodiments of the invention, the central agency that operates the central data processing system (30) or the central surveillance system (50) may provide a trusted service of generating and disseminating public/private key pairs to the different healthcare entities.

Based on the teachings herein, one of ordinary skill in the art can readily envision various system architectures that may be implemented for sharing patient data, and such architectures will vary depending on the application. For instance, the system (10) may be implemented for multiple central data processing systems (30) or surveillance systems (50) in some hierarchical manner, wherein the multiple systems (30) and (50) can have different levels of authority to re-identify patient data for different purposes, or re-identify patient data owned by particular entities, etc. More specifically, by way of example, the system (10) may be located in each of a plurality of predefined geographical locations, wherein the central surveillance system (50) in each location can use its master private key (53) to re-identify patient data for only those de-identified records maintained by the respective central systems (30). In this embodiment, another hierarchical surveillance system may have a master private key that is capable of re-identifying patient data in all geographical locations covered by the system. In this regard, nothing herein should be construed as placing a limitation on the scope of the invention. Exemplary applications for the system (10) of FIG. 1 will be described below.

It is to be appreciated that in the exemplary system of FIG. 1, a secure public/private key encryption scheme enables non-restricted, free dissemination of public keys that are used for generating de-identified patient that is stored in de-identified data records which are disclosed or otherwise shared with third party entities, while protecting patient privacy by allowing only those holders of valid private keys (e.g., owners of the patient data, or legally empowered entities) to decode the de-identified patient data and re-identify patients, when necessary. The public keys are freely distributable (no HIPAA issues) to healthcare organizations for de-identification of patient data. Moreover, the public keys can be used to produce a unique, reproducible encrypted version of patient identifying information. Since the encryption is reproducible, the same patient can be recognized at different times (i.e., consistent de-identification can be achieved over episodic collection events) even though the identity of the person remains unknown.

In other embodiments of the invention, symmetric encryption technologies (same key to encode and decode) can also be implemented in a similar manner. Indeed, for some applications, symmetric key encryption would be as efficient and secure as asymmetric (public/private key) encryption.

Systems and methods according to the invention for de-identifying patient data can be implemented for various purposes such as research, public health or healthcare operations. For example, the system (10) of FIG. 1 may be implemented for monitoring for natural or human induced disease outbreaks. In particular, a governmental agency can establish one or more centers for monitoring bioterrorism attacks. In the exemplary embodiment of FIG. 1, the central data processing system (30) may be operated by a governmental agency (central monitor) that collects de-identified patient from a plurality of different clinical sites (or other sources) within some geographical area, which have databases of identified patient data (21-1~21-n). The governmental agency can monitor for natural or human induced disease outbreaks by collecting and analyzing de-identified patient data from a plurality of different healthcare organizations while ensuring patient privacy under normal circumstances. If an outbreak is detected, the governmental agency (e.g., the CDC or other legally empowered entities) can immediately re-identify patients by using the appropriate private keys (e.g., master private key) to thereby initiate the necessary action to confine the outbreak and to increase the chances of survival of the infected individuals. If the government agency itself does the monitoring, central data processing system (30) and the central surveillance (50) may be merged. However, if the government subcontracts the monitoring they will likely remain distinct.

Systems and methods according to the present invention are advantageous for applications for monitoring for natural or human induced disease outbreaks, such as in bioterrorism. Indeed, for an application such as bioterrorism monitoring to be effective, there are two significant requirements: (1) to maintain patient privacy and comply with HIPAA, the centers should not have access to identified data and monitoring should be performed using de-identified data; and (2) to enable the governmental agency to quickly identify the individuals, if a bioterrorism attack is detected. Either requirement is easy to meet alone, but meeting both together is problematic. Systems and methods according to the invention allow both these requirements to be met simultaneously.

One traditional way to meet both requirements would be to maintain a lookup table that mapped the de-identified patient information (say patient ID) back to the identified patient information. This method may be effective in some applications, but is clearly ineffective for applications such as bioterrorism monitoring where not just the originator of the data but a central organization (government) will need to be able to re-identify information very quickly. The logistics of transporting and protecting a master lookup table are complex, expensive, and may not even be realistic.

Moreover, systems and methods according to the present invention for de-identifying patient data can be implemented for clinical trials and research studies, which is common in the medical industry. The following requirements are common for experiments and clinical trials: (1) to comply with HIPAA, analysis must be done on de-identified data when the persons analyzing patient data are not associated with the provider organization; (2) data is collected at various points of time and analyses are performed after each data collection; (3) each time data is collected, the patient should be de-identified in the same way (e.g., it is critical to know that "de-identified patient 24" from a first round of collection is also present in a second round and is still de-identified as "de-identified patient 24"); and (4) the hospital (or other provider of de-identified patient information) may or may not want the ability to re-identify the data. Such uses would probably come under the limited data set provisions of HIPAA rather than fully de-identified data.

For requirements 1, 2 and 3, systems and methods according to the present invention afford some unique advantages, and also provide advantages for requirement 4. With a conventional method of using a lookup table, the fact that the table is HIPAA protected has negative implications since the stakeholder who has requirements 2 and 3 is not the provider but the analyst. The conventional method forces the upkeep costs and responsibility for the lookup table onto the providers (who have no direct interest in those requirements 2 and 3). Further, the conventional method forces the analyst to lose control of a key artifact needed to meet their requirements. In contrast, the present invention can meet requirements 1-3, eliminate the maintenance costs to the provider, give the analysts control over all they need to meet requirements 2 and 3 (i.e., the public key), and yet ensure HIPAA compliance. The present invention ensures that even when the same patient is treated at different times, both episodes are recognized as being for the same patient (even when the data for each episode is collected at disparate times). As to requirement 4, if the hospital wants to have the option to re-identify data, it would simply have to store the private key.

Figure 3:
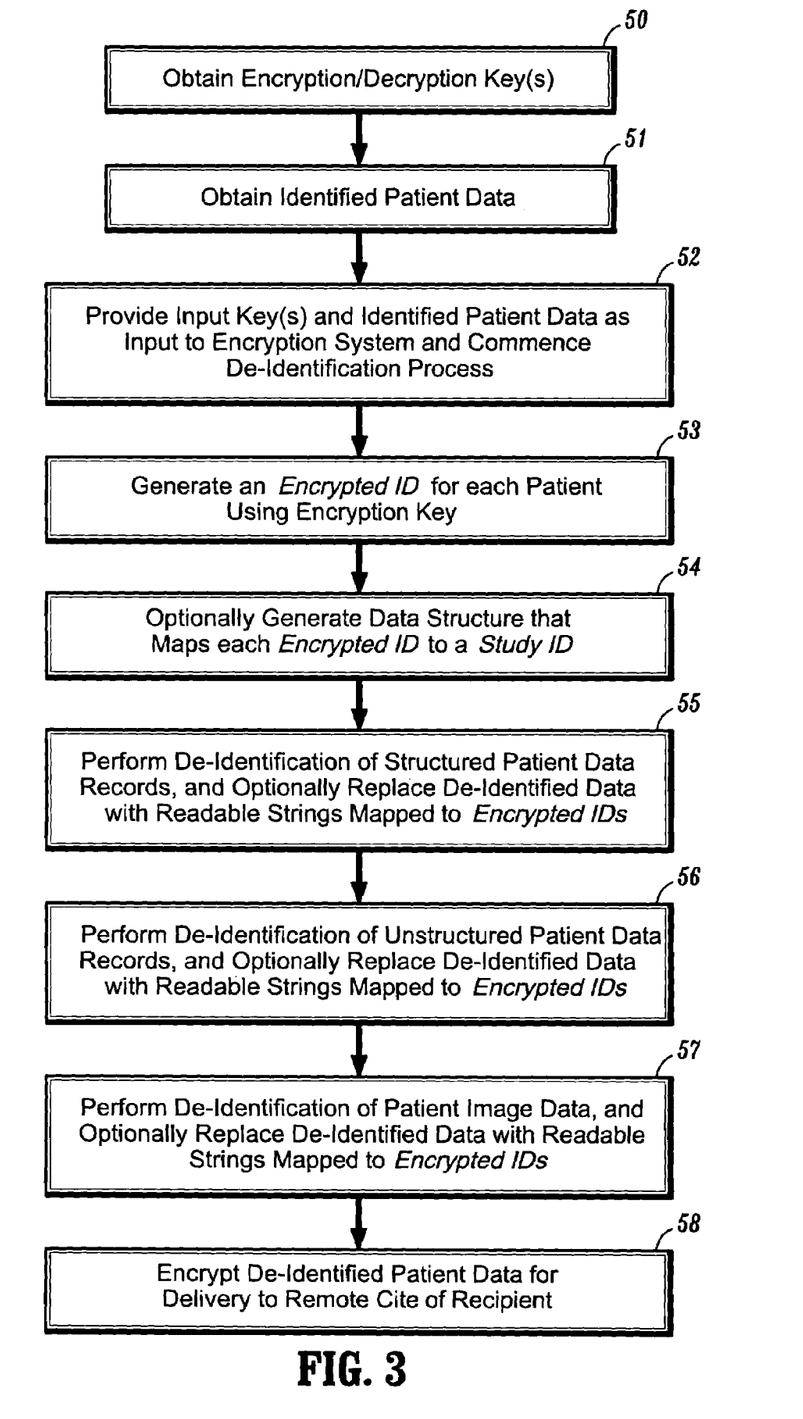
FIG. 3 is a flow diagram of a method for de-identifying patient data records according to an exemplary embodiment of the invention.

FIG. 3 is a flow diagram illustrating a method for de-identifying patient data according to an exemplary embodiment of the invention. For example, FIG. 3 illustrates a method by which one or more clinical sites (e.g., hospitals, doctors, etc.) can de-identify patient data for purposes of disclosing/distributing the de-identified patient data to one or more third-party entities (e.g., governmental agency, research agency, or medical service provider, etc,) for a particular application, while ensuring patient privacy. In one exemplary embodiment of the invention, FIG. 3 depicts an HIPAA-compliant de-identification and disclosure process. In this regard, the disclosing and receiving parties can execute a "data use agreement" or "restricted access agreement", for example, which limits the distribution of the de-identified records, whereby the recipient agrees to restrictions on who can use or receive the data and for what purposes.

Referring now to FIG. 3, a method for de-identifying patient data includes an initial step where a disclosing entity (e.g., hospital) will obtain encryption/decryption keys from a trusted entity (step 50), which are to be used for de-identifying and re-identifying patient data that is owned by the disclosing entity. In one embodiment of the invention using asymmetric key encryption, the encryption/decryption keys comprise a public/private key pair that is associated with that disclosing entity. A public key cryptographic process for generating a public/private key pair can be implemented using an asymmetric encryption method such as RSA, DSA or PGP. In another embodiment using symmetric key encryption, a private key is generated for the disclosing entity, which is used for both encrypting and decrypting patient data. As noted above, in one exemplary embodiment of the invention, the encryption keys can be generated and securely disseminated by a trusted certificate authority (CA). In another embodiment, the third-party entity that collects the de-identified data may be authorized to provide a trusted service of generating and issuing the encryption keys.

Next, the identified patient data records to be de-identified and disclosed are accessed from a database owned and operated by the disclosing entity (step 51), and the identified patient data records and encryption key are input to an encryption system (step 52) to generate de-identified patient data records. In accordance with HIPAA regulations, all de-identification of patient data records must occur at the clinical site of the disclosing party. For example, as a general rule, a third-party is not permitted to remove identified patient data records from a hospital and then de-identify the identified patient data records at a later time, but there may be exceptions to this rule. The encryption system for de-identifying the patient data records may be running on a computer at the clinical site or on a portable computing system (e.g., laptop computer) of the third-party. Under HIPAA regulations, if a laptop is used, for example, the third-party representative must remove all patient specific data and encryption keys from the laptop before leaving the hospital.

With the encryption system operating in a de-identification mode, an initial step is to use the encryption key (e.g., public key) to generate an Encrypted ID for each subject patient of the identified patient data records (step 53). As noted above, an Encrypted ID of a given patient is a unique reproducible encrypted version of patient identifying information that is sufficient to uniquely identify the patient. The patient identifying information, which is encrypted to generate the Encrypted ID, may include one or more items of patient identifying information, including, but not limited to, patient name, social security number, and/or address. The Encrypted ID for each patient is generated such that the patient identifying information contained within the Encrypted ID cannot be reconstructed without a valid decryption key (e.g. private key). The particular number and/or types of patient identifying information for generating the Encrypted IDs will vary depending on the application. In one exemplary embodiment of the invention, Encrypted IDs can be generated by encrypting the information that comprises internal patient IDs that are maintained by a hospital.

It is to be appreciated that since each Encrypted ID is a unique reproducible encrypted version of patient identifying information, the process preserves patient uniqueness to enable to the same patient to be recognized at different collection times. In other words, this process ensures that if data is collected more than once from a particular patient, the patient will be mapped to the same Encrypted ID.

Next, an optional step is performed for mapping the Encrypted IDs to corresponding Study IDs (step 54). The Encrypted IDs are not human readable and may consist of long strings (such as ASCII string, strings, byte arrays, character arrays, Unicode arrays, etc.). Therefore, in one exemplary embodiment of the invention, each Encrypted ID can be arbitrarily mapped to a unique integer (Study ID), which in turn corresponds to a short, human readable string that contains no patient information. For instance, for ease of reference, an Encrypted ID can be arbitrarily mapped to an integer, 24, which is mapped in turn to a Study ID comprising a short readable string such as "Patient #24". This mapping can be made publicly available without compromising patient privacy. Moreover, human readable replacement strings can be generated for de-identified information that is associated with a given Encrypted ID, and the replacement strings can be used to replace de-identified patient information. For example, given an Encrypted ID that includes decrypted patient information including a patient name and address, replacement strings such as "patient 24 name" and "patient 24 address", etc., could be used to replace the de-identified patient information.

A next step of the exemplary de-identification process of FIG. 3 comprises de-identifying "structured" patient data records included in the identified patient data records, and optionally replacing de-identified data elements with short readable strings associated with Encrypted IDs (step 55). As noted above, structured patient data is typically maintained in database tables, wherein the patient data elements are known a priori and can readily be searched. In general, a process of de-identifying "structured" patient data records comprises removing all database elements that include patient identifying information, that is, information that can be used to identify the subject patient of the patient data records.

In one exemplary embodiment of the invention, de-identifying is performed in accordance with the "Safe Harbor" method of the Privacy Rule, in which structured patient data elements corresponding to the 18 specified attributes in the "Safe Harbor" list are purged from the structured patient records. The 18 elements of the "Safe Harbor" list are summarized below. In another exemplary embodiment of the invention, de-identification may be performed as per the "Limited Data Set" provisions of HIPAA, which is permitted for research purposes. More specifically, by way of example, de-identification may be performed to de-identify the 18 specified attributes of the HIPAA "Safe Harbor" method with the exception of dates, as follows:

(1) Patient names are removed and a unique Encrypted ID is generated for each patient as discussed above.
(2) Zip Codes are removed or replaced as per the de-identification protocol specified by HIPAA.
(3) Dates are processed as follows:
  (i) Birth dates and Death dates are de-identified except for the year (i.e., Jul. 4, 1955 will be converted to Jan. 1, 1955). All ages 81 and over will be converted to 81. Although the HIPAA requirement is 89, 81 can be selected to ensure HIPAA compliance, even if data collection continues for 8 years. Beyond 8 years, a new protocol will need to be developed; and
  (ii) All treatment-related dates (e.g., admission date, discharge data, procedure date, and visit data) are optionally not de-identified, which is permissible under the HIPAA "limited data set" measures or may be removed or replaced with non-identifying equivalent. This could include methods where the number of days, hours, or seconds between dates for the patient is preserved but the dates themselves are altered.
(4) Telephone numbers are removed or replaced with a non-identifying equivalent (e.g., "patient24phonenum")
(5) Fax numbers are removed or replaced with a non-identifying equivalent.
(6) Electronic mail addresses are removed or replaced with a non-identifying equivalent.
(7) Social Security numbers are removed or replaced with a non-identifying equivalent.
(8) Medical record numbers are removed or replaced with a non-identifying equivalent.
(9) Health plan beneficiary numbers are removed, but Insurance company information may be retained or replaced with a non-identifying equivalent.
(10) Account numbers are removed or replaced with a non-identifying equivalent.
(11) Certificate/license numbers are removed or replaced with a non-identifying equivalent.
(12) Vehicle identifiers and serial numbers, including license plate numbers, are removed or replaced with a non-identifying equivalent.
(13) Device identifiers and serial numbers are removed or replaced with a non-identifying equivalent.
(14) Web Universal Resource Locators (URLs) are removed or replaced with a non-identifying equivalent.
(15) Internet Protocol (IP) address numbers are removed or replaced with a non-identifying equivalent.
(16) Biometric identifiers, including finger and voice-prints, are removed or replaced with a non-identifying equivalent.
(17) Full face photographic images and any comparable images are removed.
(18) Any other unique identifying numbers, characteristics, or codes are removed or replaced with a non-identifying equivalent.

Essentially, in the above exemplary embodiment, the patient identifying information of element 3(ii) (dates) is the only difference from the "Safe Harbor" set provided by HIPAA. As noted above, this is permissible under HIPAA's "Limited Data Set" for purposes of research. HIPAA requires that the third-party entity agree to a Data Use Agreement to meet with the "Limited Data Set" requirements.

A de-identification process for a structured data record for a given patient results in the creation of a de-identified structured patient record, which includes a corresponding Encrypted ID or replacement string such as "patient 24 ID" that is mapped to the Encrypted ID, which is stored in the de-identified structured patient record. Moreover, the de-identified structured patient record may include one or more replacement strings for de-identified patient information.

A next step in the de-identification process is to de-identify unstructured patient data records such as radiology reports, which are included in the identified patient data records, and optionally replace de-identified data with replacement strings associated with Encrypted IDs (step 56). In general, one exemplary process for de-identifying unstructured patient data records includes performing a text string search using any suitable keyword searching application to locate various keywords (which are associated with identified patient information) within text documents to be de-identified. For example, all text strings within text documents, such as patient names, physician names, and patient-specific identification numbers or information, can be located, removed and possibly replaced with generic text strings as desired or required by law.

More specifically, in one exemplary embodiment, de-identification of unstructured patient records includes removing all patient-specific text strings that correspond to patient information contained in elements (2) and (4) through (18) of the "Safe Harbor" set, as outlined above. This process is applied to patient-specific information (for elements (2) and (4) through (18)), which is stored in corresponding structured patient records. For example, for medical records of a given patient, a set of text strings that are to be located in the text data can be generated from the corresponding structured databases, which are used for searching the unstructured patient data to find matching text strings that will be eliminated from the text.

Additionally, text strings of patient names can be de-identified in various manners. For instance, internal patient IDs or names can be replaced with a corresponding Study ID associated with an Encrypted ID using the mapping as discussed above. Further, a string of a patient name can be replaced with a de-identified name, which will remove all common variations of a name. For example, if a patient's name is John James Smith, then text strings such as "John", "Smith", "John Smith", "John J. Smith", and "John James Smith", for example, can be removed. Furthermore, de-identification of unstructured patient data may include searching for name prefixes such as Dr., Mrs., Mr., Ms., Fr., etc, and de-identify the name that follows.

In yet another embodiment, a hospital, for example, can provide templates that are used in the unstructured data that contains identified information (e.g., if a note ends with "Doctors Initials: JJS"), and this information can also be de-identified. If the third-party discovers any such information while working with the data, this will also be de-identified. All treatment-related dates will not be de-identified as discussed previously.

A de-identification process for an unstructured data record for a given patient can result in the creation of a de-identified unstructured patient record, which includes a corresponding Encrypted ID or replacement string mapped to the Encrypted ID, which is stored in the de-identified unstructured patient record. Moreover, the de-identified unstructured patient record may include replacement strings for de-identified patient data as discussed above.

The exemplary de-identification process depicted in FIG. 3 further comprises de-identifying patient image data, and optionally replacing de-identified data with readable strings associated with the Encrypted IDs (step 57). In general, in one exemplary embodiment, all DICOM fields containing patient-specific information are removed using the method described above for de-identifying structured patient data records. The de-identification process adds DICOM fields for Encrypted IDs (or corresponding Study ID strings) and other needed structured fields as per the structured data de-identification protocol described above. In addition, dates of birth/death are also de-identified as discussed above.

Further, any "burned-in" patient data on the image will be erased/obscured, including, for example, names, dates, institutions, and any other identifying marks. This is necessary because some modalities, such as ultrasound, do not generally use "overlay" features of DICOM. Thus, removal of "burned in" identifying patient data is performed in a manual, or semi-automated, fashion using any suitable program such as Showcase, which can blank out parts of an image. Moreover, any text reports related to the images are de-identified as per the protocol for de-identifying patient unstructured text as described above.

After the de-identification process is complete, the de-identified data records are optionally encrypted for transport from the clinical site to the central data processing system (step 58). The de-identified data may be securely transmitted from the clinical site to the central system by a communications network, wherein the de-identified patient data records are stored in a database on a computer behind a firewall.

It is to be appreciated that the flow diagram of FIG. 3 is merely exemplary, and that the particular order of steps 55, 56, and 57 is not significant to the invention and is arbitrary. One or more of these steps can be left out if the produced data is not needed.

Although illustrative embodiments of the present invention have been described herein with reference to medical information processing systems in the accompanying drawings, it is to be understood that the invention is not limited to those precise embodiments, and that one of ordinary skill in the art could readily envision other applications for the present invention in which secured encryption can be used to share any type of protected or private information, while maintaining individual privacy. For instance, secured encryption schemes as described herein could be used for enabling schools or colleges or educational agencies, for example, to share student records for any desired application. Moreover, the invention may be applied to enable sharing of employer or employee records, performance appraisals, etc. Other various other changes and modifications may be affected therein by one skilled in the art without departing from the scope or spirit of the invention.

What is claimed is:

1. A method for processing data, comprising the steps of:
   obtaining a patient data record of a patient which includes patient identifying information;
   removing the patient identifying information from the patient data record to generate a de-identified data record comprising unencrypted patient data in the patient data record which does not identify the patient;
   generating an encrypted ID for the patient, wherein the encrypted ID comprises an encrypted representation of one or more items of patient identifying information; and storing the encrypted ID with or in the de-identified data record,
wherein the step of removing the patient identifying information in the patient data record includes automatically removing patient identifying information from an unstructured data record by locating a text string in the unstructured data records that includes patient identifying information, and removing the text string from the unstructured data record, wherein the text string to be removed from the unstructured data record is determined based on a matching text string that is included in a database element of a structured data record associated with the unstructured data record.

2. The method of claim 1, wherein the step of generating an encrypted ID for the patient comprises encrypting the one or more items of patient identifying information using a public key.

3. The method of claim 1, further comprising securely maintaining a decryption key, which can be accessed by an authorized entity to decrypt the encrypted ID in the de-identified data record to re-identify the patient.

4. The method of claim 3, wherein the decryption key is a private key that is associated with the public key for encryption.

5. The method of claim 3, wherein the decryption key is a master private key that can decrypt de-identified data produced from many encryption/decryption key pairs.

6. The method of claim 1, wherein the step of removing the patient identifying information in the patient data record to generate a de-identified data record is performed in compliance with a Safe Harbor rule or Limited Data set Rule of HIPAA.

7. The method of claim 1, wherein the step of removing the patient identifying information in the patient data record includes automatically removing patient identifying information from a structured data record.

8. The method of claim 6, wherein the step of removing the patient identifying information from the patient data record comprises removing database elements that contain the patient identifying information.

9. The method of claim 1, wherein the step of removing the patient identifying information from the patient data record includes automatically removing patient identifying information from an image.

10. The method of claim 9, wherein the step of automatically removing patient identifying information from an image comprises removing patient identifying information contained in structured fields.

11. The method of claim 9, wherein the step of automatically removing patient identifying information from an image comprises manually identifying burned-in patient identifying information within an image and automatically blanking the identified patient identifying information.

12. The method of claim 1, further comprising the steps of:
mapping the encrypted ID to a Study ID that comprises an arbitrary human readable ID which contains no patient identifying information; and
generating a data structure that includes the mapping.

13. The method of claim 12, further comprising mapping the Study ID to one or more replacement strings that can be used to replace de-identified data in the de-identified data record.

14. The method of claim 12, further comprising making the data structure publicly accessible.

15. The method of claim 12, further comprising using the encrypted ID or corresponding Study ID to recognize a subject patient of patient data records collected at different times.

16. The method of claim 1, wherein the method is implemented for sharing patient data for purposes of research.

17. The method of claim 1, wherein the method is implemented for sharing patient data for purposes of central monitoring for natural or human induced disease outbreaks.

18. A program storage device readable by a machine, tangibly embodying a program of instructions executable on the machine to perform method steps for processing medical information, the method steps comprising:
obtaining a patient data record of a patient which includes patient identifying information;
removing the patient identifying information from the patient data record to generate a de-identified data record comprising unencrypted patient data in the patient data record which does not identify the patient;
generating an encrypted ID for the patient, wherein the encrypted ID comprises an encrypted representation of one or more items of patient identifying information; and
storing the encrypted ID with or in the de-identified data record,
wherein the instructions for removing the patient identifying information in the patient data record comprise instructions for automatically removing patient identifying information from an unstructured data record by locating a text string in the unstructured data records that includes patient identifying information and removing the text string from the unstructured data record, wherein the text string to be removed from the unstructured data record is determined based on a matching text string that is included in a database element of a structured data record associated with the unstructured data record.

19. The program storage device of claim 18, wherein the instructions for generating an encrypted ID for the patient comprise instructions for encrypting the one or more items of patient identifying information using a public key.

20. The program storage device of claim 18, further comprising instructions for securely maintaining a decryption key, which can be accessed by an authorized entity to decrypt the encrypted ID in the de-identified data record to re-identify the patient.

21. The program storage device of claim 20, wherein the decryption key is a private key that is associated with the public key for encryption.

22. The program storage device of claim 20, wherein the decryption key is a master private key that can decrypt de-identified data produced from many encryption/decryption key pairs.

23. The program storage device of claim 18, wherein the instructions for removing the patient identifying information in the patient data record to generate a de-identified data record is performed in compliance with a Safe Harbor rule or Limited Data set Rule of HIPAA.

24. The program storage device of claim 18, wherein the step of removing the patient identifying information in the patient data record includes automatically removing patient identifying information from a structured data record.

25. The program storage device of claim 24, wherein the instructions for automatically removing patient identifying information from a structured data record comprise instructions for removing database elements that contain patient identifying information.

26. The program storage device of claim 18 wherein the instructions for removing the patient identifying information in the patient data record comprise instructions for automatically removing patient identifying information from an image.

27. The program storage device of claim 26, wherein the instructions for automatically removing patient identifying information from an image comprise instructions for removing patient identifying information contained in structured fields.

28. The program storage device of claim 18, farther comprising instructions for performing the steps of: mapping the encrypted ID to a Study ID that comprises an arbitrary human readable ID which contains no patient identifying information; and generating a data structure that includes the mapping.

29. The program storage device of claim 28, further comprising instructions for mapping the Study ID to one or more replacement strings that can be used to replace de-identified data in the de-identified data record.

30. A method for processing data, comprising the steps of:
obtaining a data record of an individual which includes individual identifying information;
removing the individual identifying information from the data record to generate a de-identified data record comprising unencrypted data in the data record which does not identify the individual;
generating an encrypted ID for the individual, wherein the encrypted ID comprises an encrypted representation of one or more items of individual identifying information; and
storing the encrypted ID with or in the de-identified data record,
wherein the step of removing the individual identifying information from the data record includes automatically removing the individual identifying information from an unstructured data record by locating a text string in the unstructured data records that includes the individual identifying information, and removing the text string from the unstructured data record, wherein the text string to be removed from the unstructured data record is determined based on a matching text string that is included in a database element of a structured data record associated with the unstructured data record.

31. The method of claim 30, wherein the data record comprises medical information.

32. The method of claim 30, wherein the data record comprises financial information.

33. The method of claim 30, further comprising securely maintaining a decryption key, which can be accessed by an authorized entity to decrypt the encrypted ID in the de-identified data record to re-identify the individual.

* * * * *